(12) United States Patent
Kraus

(10) Patent No.: US 6,372,913 B1
(45) Date of Patent: Apr. 16, 2002

(54) PROCESS FOR PREPARING 2-SUBSTITUTED 5-FORMYLTHIAZOLES

(75) Inventor: Helmut Kraus, Odenthal (DE)

(73) Assignee: Bayer AG, Leverkusen (DE)

( * ) Notice: Subject to any disclaimer, the term of this patent is extended or adjusted under 35 U.S.C. 154(b) by 0 days.

(21) Appl. No.: 09/135,134

(22) Filed: Aug. 17, 1998

(51) Int. Cl.⁷ .......................................... C07D 277/24
(52) U.S. Cl. .................................................... 548/188
(58) Field of Search ........................................ 548/188

(56) References Cited

FOREIGN PATENT DOCUMENTS

| BE | 612839 | 1/1962 | |
|---|---|---|---|
| DE | 1147584 | 4/1963 | |
| DE | 1182234 | * 11/1964 | ................ 548/188 |
| EP | 0 125 094 | 11/1984 | |
| WO | WO 97/22599 | 6/1997 | |

OTHER PUBLICATIONS

Metzger Thiazoles & its Derivatives pt. 1 pp. 258–269, Mar. 1979.*

Hantzsch: Über die Oxy–thiazole oder Thiazolone, *Chem. Ber.* 60, pp. 2537–2545, (1927).

* cited by examiner

*Primary Examiner*—Joseph K. McKane
*Assistant Examiner*—Sonya N. Wright
(74) *Attorney, Agent, or Firm*—Brinks Hofer Gilson & Lione

(57) ABSTRACT

2-substituted 5-formylthiazoles are prepared in an advantageous manner by reacting halogenomalonaldehydes in the presence of a solvent and a $C_1$-compound of the formula (III)

(III)

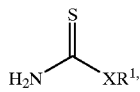

in which

X represents oxygen or sulfur and $R^1$ is as defined in the description, the reaction mixture comprising less than 5% by weight of water.

8 Claims, No Drawings

PROCESS FOR PREPARING 2-SUBSTITUTED 5-FORMYLTHIAZOLES

The present invention relates to an improved process for preparing 2-substituted 5-formylthiazoles.

2-substituted 5-formylthiazoles are important intermediates for the preparation of crop protection agents (see, for example, EP-A-395 174).

It is known to prepare 4-substituted 2-alkoxy- or 2-thioalkyl-thiazoles starting from halogenoketones and appropriate $C_1$-building blocks (see Chem. Ber. 60, 2537 (1927)). For the corresponding preparation of 5-substituted thiazoles, the relatively unstable α-halogenoaldehydes would be required instead of the stable α-halogenoketones. This usually leads to reduced yields.

2-amino-5-formylthiazole is obtainable in low yields in aqueous solution from 2-chloromalonaldehyde and thiourea (see DE-A-1 182 234). According to EP-A-125 094, 2-thiomethyl-5-formylthiazole was also obtained in a similar manner; however, a description of the process and yields were not given.

This invention, accordingly, provides a process for preparing 2-substituted 5-formylthiazoles of the formula

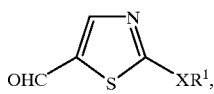
(I)

in which

X represents oxygen or sulfur and $R^1$ represents $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl, $C_6$–$C_{12}$-aryl or $C_7$–$C_{14}$-aralkyl, which comprises reacting halogenomalonaldehydes which correspond in a tautomeric form to the formula (II)

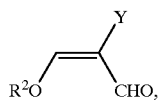
(II)

in which

Y represents fluorine, chlorine, bromine or iodine and $R^2$ represents hydrogen, an alkali metal or an equivalent of an alkaline earth metal, in the presence of a solvent with a $C_1$-compound of the formula (III)

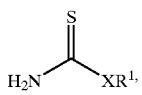
(III)

in which

X and $R^1$ are each as defined under formula (I), the reaction mixture comprising less than 5% by weight of water.

In the formulae (I) and (III), $R^1$ preferably represents $C_1$–$C_8$-alkyl. In formula (II), Y preferably represents chlorine or bromine and $R^2$ preferably represents an alkali metal, in particular sodium.

Compounds of the formula (II) can be prepared in a known manner or analogously thereto, for example from the corresponding aminoethylene compounds (see, for example, J. Org. Chem. 28,3249 (1963) and Example 4).

Compounds of the formula (III) where X=oxygen (=xanthogenamides or thiocarbamic acid O-esters) can also be prepared in a known manner or analogously thereto, for example from ammonium thiocyanate, an alcohol $R^1OH$ and sulfuric acid (see, for example, Chem. Ber. 115, 1252 (1982)).

Compounds of the formula (III) where X=sulfur (=dithiocarbamic acid esters) can likewise be prepared in a known manner or analogously thereto, for example from ammonium thiocarbamate and an alkylating agent containing a group $R^1$ (see, for example, Synthesis 1985, 948).

It is possible to use, for example, 0.9 to 1.25 mol of a compound of the formula (III) per mole of a compound of the formula (II). This amount is preferably from 1 to 1.1 mol. Attention is drawn to the fact that here and elsewhere in this text, reference to a compound of the formula (II) also includes the other possible tautomeric form of this compound.

Suitable solvents for the process according to the invention are, for example, ethers such as tetrahydrofuran, diethyl ether and methyl tert-butyl ether, alcohols such as ethanol and isopropanol, esters such as ethyl acetate and propyl acetate, nitriles such as acetonitrile, chlorinated hydrocarbons such as methylene chloride, di-, tri- and tetrachloroethane and chlorobenzenes and carboxylic acids such as formic acid, acetic acid and propionic acid. It is also possible to employ mixtures of solvents. Based on 100 g of a compound of the formula (II), it is possible to employ, for example, 50 to 1000 g of solvent.

If compounds of the formula (II) are employed where $R^2$=alkali metal or alkaline earth metal, preference is given to using, as solvents, carboxylic acids, in particular formic acid or acetic acid, for example from 1 to 5 mol of carboxylic acid per mole of a compound of the formula (II).

If the solvent used is a carboxylic acid, preference is given to buffering this by addition of a buffer salt. Preferred buffer salts are alkali metal salts of the carboxylic acid which is employed in each case. Particular preference is given to using formic acid/sodium formate and acetic acid/sodium acetate. It is possible to use, for example, from 0.5 to 5 mol of buffer salt per mole of carboxylic acid.

The process according to the invention can be carried out, for example at temperatures in the range from −20 to +80° C. Preference is given to temperatures from ±0 to +65° C.

It is an essential feature of the process according to the invention that it is carried out in the presence of less than 5, in particular less than 2% by weight of water (based on the total reaction mixture). It is advantageous to minimize the water content as far as this is possible with justifiable expenditure, for example to a content of less than 0.01% by weight (based on the total reaction mixture). The removal of the last portions of water frequently requires very high expenditure, with may not be reasonable economically. The reagents and auxiliaries required are therefore generally employed in dried form, but not necessarily in totally anhydrous form. Prior to use, the compound of the formula (II) is preferably substantially dehydrated by drying. Likewise, the compound of the formula (III) employed or the solution thereof should be substantially anhydrous. If formic acid is employed, it may contain a maximum of 4% by weight of water. Preferably, it contains a maximum of 0.3 to 3% by weight of water.

The process according to the invention can be carried out, for example, by initially charging the compound of the formula (II) in a suitable solvent and adding the compound of the formula (III) dropwise dissolved in a suitable solvent or in molten form.

The reaction mixture which is present after the process according to the invention has been carried out can be worked up, for example, by removing its solid components, for example by filtration. The crude solution which is then present can be concentrated and, if appropriate, the concentrate neutralized, and then extracted with a suitable solvent, for example dichloromethane. After clarification, concentration of the extract and a crystallization, the 2-substituted 5-formylthiazole of the formula (I) which has been prepared can be obtained in purities of 90% or more.

A particularly preferred embodiment of the present invention comprises reacting sodium chloromalonaldehyde in formic acid/sodium formate or acetic acid/sodium acetate with, if appropriate, dissolved xanthogenamide or 5-alkyl dithiocarbonate in the presence of 0.5 to 2% by weight of water (based on the total reaction mixture). This generally leads to reaction yields of 2-substituted 5-formylthiazoles of the formula (I) in the range from 65 to 90% of theory. The isolated yields can then be, for example in the range from 55 to 80% of theory.

The process according to the invention affords 2-substituted 5-formylthiazoles in a simple, reproducible manner in good yields.

EXAMPLES

Example 1

64.3 g of sodium chloromalonaldehyde (obtained according to Example 4) and 34 g 5 of sodium formate were initially charged in 300 ml of formic acid, and a solution of 50.5 g of ethylxanthogenamide in 300 ml of ethyl acetate was added dropwise at 20° C. The reaction mixture contained 1.5% by weight of water. The reaction mixture was stirred overnight and then concentrated on a rotary evaporator at 20 mbar and a bath temperature of 50° C., admixed with 200 ml of water and adjusted to pH 5 using aqueous sodium hydroxide solution. The mixture was subsequently extracted with methylene chloride and clarified using Celite® and Tonsil®. Concentration gave 66.9 g of an oil which slowly crystallized. The product was 2-ethoxy-5-formylthiazole of a melting point (MTBE) of 66.5° C.

$^1$NMR (CDCl$_3$): 1.48 (t, 3H); 4.57 (q, 2H); 7.84 (s, 1H); 9.82 (s, 1H) ppm $^{13}$C NMR: 182.4; 180.8; 149.4; 133.0; 69.5; 14.7 ppm Example 2

By the method of Example 1, 0.5 mol of sodium chloromalonaldehyde was reacted with 0.5 mol of S-methyl dithiocarbamate, the water content of the reaction mixture being 1.8%. 2-thiomethyl-5-formylthiazole of melting point 82° C. was obtained in a yield of 88% of theory.

$^1$H NMR (CDCl$_3$): 2.75 (s, 3H); 8.21 (s, 1H); 9.90 (s, 1H) ppm $^{13}$C NMR: 181.8; 178.7; 152.6; 139.5; 17.6 ppm Example 3

3.44 g of sodium bromomalonaldehyde and 1.36 g of sodium formate were initially charged in 30 ml of formic acid, and 9 g of molten ethylxanthogenamide were added dropwise at 10° C. The reaction mixture contained 1.2% by weight of water. Th mixture was stirred at room temperature for 20 hours and then worked up by the method of Example 1, giving 2-ethoxy-5-formylthiazole in a yield of 73% of theory.

Example 4

Preparation of the Starting Material Sodium Chloromalonaldehyde (Not According to the Invention)

134 g of 3-dimethylaminochloroacrolein and one equivalent of sodium hydroxide solution were heated at 70° C. for 1 hour. After cooling, the precipitate was filtered off and washed with ethanol. This gave sodium chloromalonaldehyde trihydrate. This was dried in a drying cabinet at 100° C. and 300 mbar for 1 hour.

$^1$H NMR (d-DMSO): 8.6 ppm (s).

What is claimed is:

1. A process for preparing a 2-substituted 5-formylthiazole of the formula (I)

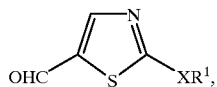

(I)

in which

X represents oxygen or sulfur and

R$^1$ represents C$_1$–C$_8$-alkyl, C$_3$–C$_8$-alkenyl, C$_2$–C$_8$-alkoxyalkyl, C$_4$–C$_8$-alkoxyalkenyl, C$_3$–C$_8$-cycloalkyl, C$_6$–C$_{12}$-aryl or C$_7$–C$_{14}$-aralkyl, which comprises reacting a halogenomalonaldehyde which corresponds in a tautomeric form to the formula (II)

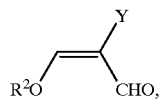

(II)

in which

Y represents fluorine, chlorine, bromine or iodine and

R$^2$ represents hydrogen, an alkali metal or an equivalent of an alkaline earth metal, in the presence of a solvent with a C$_1$-compound of the formula (III)

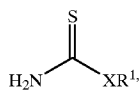

(III)

in which

X and R$^1$ are each as defined under formula (I), the reaction mixture comprising less than 5% by weight, based on the total weight of solvent, of water.

2. The process as claimed in claim 1, wherein the reaction mixture comprises less than 2% by weight, based on the total weight of solvent, of water.

3. The process as claimed in claim 1, wherein in the formulae (I) and (III) R$^1$ represents C$_1$–C$_8$-alkyl and in the formula (II) Y represents chlorine or bromine and R$^2$ represents an alkali metal.

4. The process as claimed in claim 1, wherein 0.9 to 1.25 mol of a compound of the formula (III) are employed per mole of a compound of the formula (II).

5. The process as claimed in claim 1, wherein the solvent used is selected from the group consisting of ethers, alcohols, esters, nitriles, chlorinated hydro-carbons, carboxylic acids and amines.

6. The process as claimed in claim 1, wherein the solvent is a carboxylic acid when $R^2$ is an alkali metal or alkaline earth metal.

7. The process as claimed in claim 6, wherein a salt buffer is added.

8. The process as claimed in claim 1, wherein the process is carried out a temperatures in the range from −20 to +80° C.

* * * * *